(12) United States Patent
Tarro

(10) Patent No.: US 6,989,159 B2
(45) Date of Patent: Jan. 24, 2006

(54) PHARMACEUTICAL COMPOSITIONS CONTAINING LITHIUM CARBONATE

(75) Inventor: Giulio Tarro, Naples (IT)

(73) Assignee: JDS Pharmaceuticals, LLC, New York, NY (US)

( * ) Notice: Subject to any disclaimer, the term of this patent is extended or adjusted under 35 U.S.C. 154(b) by 0 days.

(21) Appl. No.: 10/343,997

(22) PCT Filed: Aug. 6, 2001

(86) PCT No.: PCT/EP01/09054

§ 371 (c)(1),
(2), (4) Date: Jul. 28, 2003

(87) PCT Pub. No.: WO02/11740

PCT Pub. Date: Feb. 14, 2002

(65) Prior Publication Data

US 2004/0013746 A1    Jan. 22, 2004

(30) Foreign Application Priority Data

Aug. 10, 2000 (IT) .......................... MI2000A1868
Feb. 14, 2001 (IT) .......................... MI2001A0299

(51) Int. Cl.
A61K 33/00 (2006.01)
A61K 9/14 (2006.01)
A61K 9/22 (2006.01)
A61K 9/52 (2006.01)
A61P 25/18 (2006.01)

(52) U.S. Cl. ...................... 424/715; 424/457; 424/458; 424/461; 424/462; 424/468; 424/480; 424/490; 424/491; 424/492; 424/493; 424/494; 424/495; 424/496; 424/497; 514/951; 514/964

(58) Field of Classification Search ........ 424/457–458, 424/461–462, 468, 490–497, 715, 480; 514/964, 514/951

See application file for complete search history.

(56) References Cited

U.S. PATENT DOCUMENTS 4,264,573 A    4/1981  Powell et al.
4,968,505 A   11/1990  Okada et al.
5,322,698 A    6/1994  Kovacs et al.

FOREIGN PATENT DOCUMENTS

EP    396425    * 11/1990
GB    2 016 922    9/1979

OTHER PUBLICATIONS

Gai, M.N. et al., "Evaluation of the in vitro and in vivo performance of two-sustained-release lithium carbonate matrix tablets . . . " Drug Development and Industrial Pharmacy, vol. 25(2), 1999, pp. 131-140.*

Rafiee-Tehrani M. et al., "Formulation of Controlled Release Lithium Carbonate Tablets By Fluid Bed Technique," European Journal of Pharmaceutics and Biopharmaceutics, Elsevier Science Publishers B.V., Amsterdam, NL, vol. 39, No. 2, Apr. 1, 1993 pp. 87-91, XP000363223 ISSN: 0939-6411.

* cited by examiner

*Primary Examiner*—John Pak
(74) *Attorney, Agent, or Firm*—Irving M. Fishman

(57) ABSTRACT

Once daily pharmaceutical compositions containing lithium carbonate in the form of coated granules.

9 Claims, 5 Drawing Sheets

PHARMACEUTICAL COMPOSITIONS CONTAINING LITHIUM CARBONATE

Figure 1:
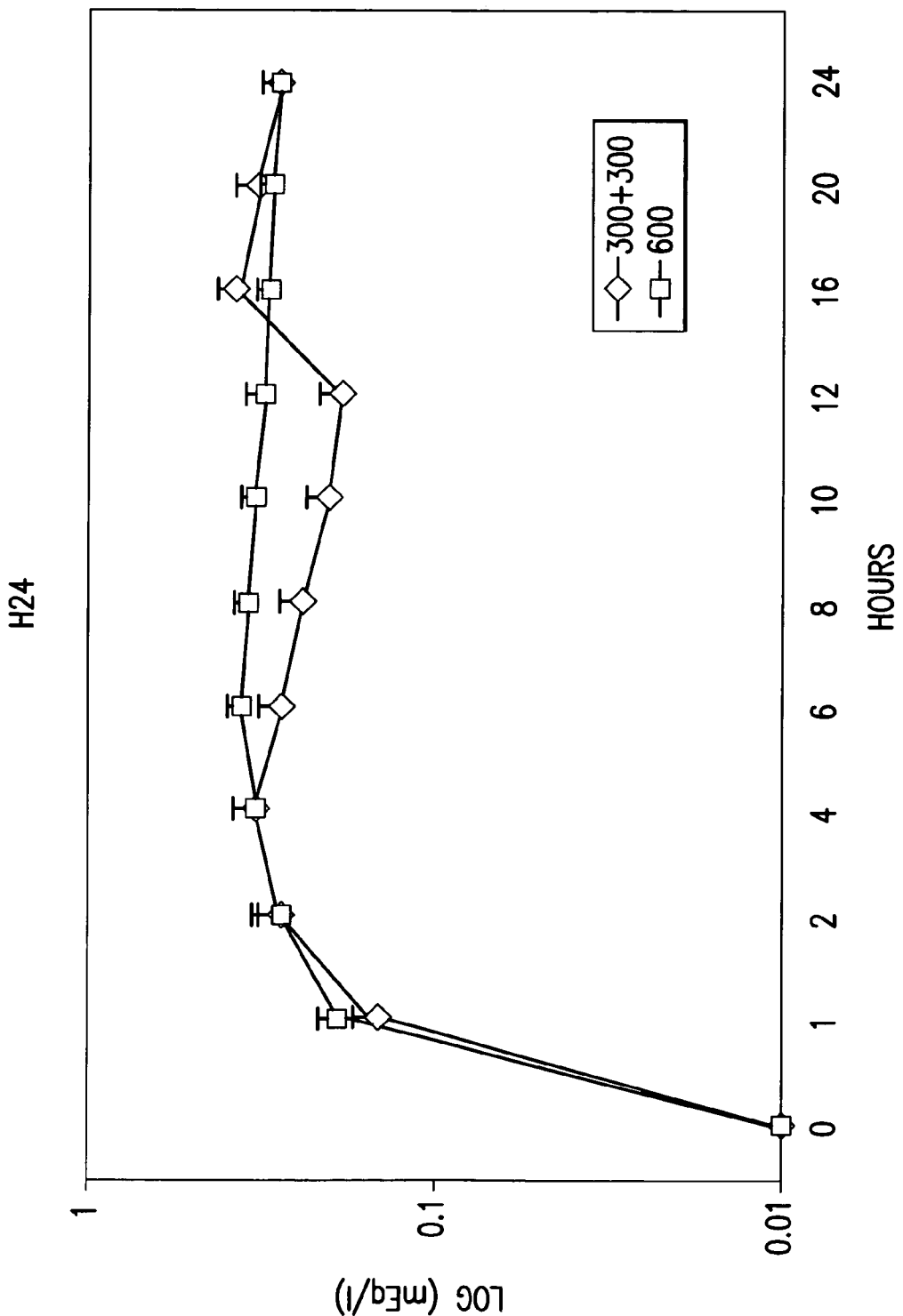

This application is a 371 of PCT/EP01/09054, filed on Aug. 6, 2001.

The present invention relates to a "Once-a-Day" lithium carbonate formulation.

The use of lithium salts in the treatment of depressive and manic disorders, psychosis, some types of cephalalgia, has been known for many years. One of the major drawbacks related with lithium therapy is its low therapeutic index on the one hand, and the need to ensure constant therapeutically useful concentrations, below the toxicity levels, on the other. An appropriate therapeutic regimen can be obtained with the preparations commercially available at present, carrying out two to three daily administrations. Lithium carbonate is completely absorbed in the gastrointestinal tract in about 8 hours, the plasma concentration peak being between, 2 and 4 hours. After being absorbed, the cation is slowly distributed inside the cells of different organs and its distribution volume approaches 1 (0.7–0.9), reaching the steady state at a concentration in the liquor below 50% compared with the plasmatic one. The starting half-life, after the first administration, is reduced by the redistribution. The plasma half-life at the steady state is 20–24 hours. More than 95% of lithium is eliminated through urine; like sodium, 80% thereof is reabsorbed in the proximal convoluted tubule and has clearance corresponding to about 20% of that of the creatinine. The lower the peak lithium concentration in the plasma, the steadier its elimination. It is therefore desirable to have controlled release formulations to decrease the number of daily administrations and the value of the plasma peaks, thus avoiding to attain toxic concentrations while increasing the patient compliance.

The present invention relates to a "Once-a-Day" controlled release formulation of lithium carbonate which fulfils the pharmacokinetic requirements mentioned above, ensuring a constant plasma concentration over the 24 hours at levels compatible with the established safety margins. The composition of the invention is in the form of a coated granulate and has the following contents, expressed in % by weight: lithium carbonate 93%, ethylcellulose 1.7%, talc 0.8%, polyvinylpyrrolidone 4.5%. The granules can be coated with known techniques, preferably with the fluidized bed technique by spraying a solution of the coating agent (ethylcellulose) in ethanol, acetone and water on the active ingredient granules. The coated granules are then incorporated in a suitable carrier for the oral administration. Hard-gelatin capsules are the most preferred administration forms. Capsules are prepared according to conventional techniques, for example as described in Remington's Pharmaceutical Sciences Handbook, Mack Pub. Co., NY, USA, XVII Ed. In addition to gelatin and any dyes, the capsules can contain sodium lauryl sulfate and magnesium stearate, as solubilizer and diluent respectively.

The coated granules, incorporated in a suitable carrier, preferably in hard-gelatin capsules, ensure a constant release rate of the active ingredient over the 24 hours, without giving raise to the plasma absorption peaks usually observed after lithium administration.

In a typical dissolution test carried out on six formulation samples, using a pH 1.1 solution in a flow-through dissolution apparatus (25 ml/min, 37° C.), the following release percentages over the 24 hours were obtained:

TABLE

| | Release percentages | | | | | | | | | |
|---|---|---|---|---|---|---|---|---|---|---|
| Hrs | Samp. 1 | Samp. 2 | Samp. 3 | Samp. 4 | Samp. 5 | Samp. 6 | Mean | Min | Max | CV |
| 1 | 9.1 | 8.5 | 8.5 | 8.9 | 9.2 | 8.9 | 8.9 | 8.5 | 9.2 | 3.33 |
| 4 | 38.7 | 34.2 | 35.3 | 36.8 | 38.2 | 36.5 | 36.6 | 34.2 | 38.7 | 4.65 |
| 8 | 59.4 | 59.1 | 59.7 | 62.2 | 65.1 | 62.4 | 61.3 | 59.1 | 65.1 | 3.82 |
| 12 | 69.8 | 69.4 | 69.9 | 73.4 | 76.8 | 72.1 | 71.9 | 69.4 | 76.8 | 3.98 |
| 16 | 82.8 | 83.6 | 84 | 88.2 | 90.1 | 87.9 | 86.1 | 82.8 | 90.1 | 3.49 |
| 24 | 90 | 93.3 | 91.6 | 94.3 | | 95.7 | 93.0 | 90 | 95.7 | 2.41 |

The data reported in the table clearly show the constant release rate of the active ingredient over the whole tested time.

Bioequivalence studies in comparison with a commercially available composition (CARBOLITHIUM®) containing lithium carbonate granules in microcapsules consisting of magnesium stearate, gelatin, titanium dioxide, indigotin, lactose, starch, methylcellulose, have been carried out. The results, reported in the following examples, clearly show that the lithium plasma concentration remains constant over 24 hours after administration of the composition of the invention, avoiding the absorption peaks observed with the comparison formulation.

The particularly favourable pharmacokinetic allows the administration of a single daily dose, remarkably increasing the patient compliance. The envisaged dosages for the active ingredient can range from a minimum of 300 mg to a maximum of 900 mg, depending on a number of factors such as the severity of the disorder to treat, the age, weight and conditions of the patient. Dosages of 300, 450 or, preferably, 600 mg of lithium carbonate in a single daily dose ensure optimal results.

The "Once-a-Day" (in the following: OaD) composition of the present invention will be used in the treatment of all those disorders which require the administration of lithium, such as depressive and manic conditions, psychosis, cephalalgia, drug leukopenia, hemopoietic diseases, immunologic diseases, AIDS (in combination with AZT) and as antitumor agent.

The following examples illustrate the invention in greater detail.

EXAMPLE 1

Standard Amounts for Manufacturing 250,000 Capsules of 600 mg Lithium Carbonate Controlled Release Capsules

| | |
|---|---|
| Lithium Carbonate | 150 Kg |
| Povidone | 7.300 Kg |
| Ethylcellulose | 2.575 Kg |
| Talc | 1.125 Kg |
| Acetone* | q.s. |

-continued

| Denaturated ethanol* | q.s. |
|---|---|
| Water* | q.s. |

*solvents used in the manufacturing process.

Preparation of the Binder Solution

Water is placed in a stainless steel container equipped with pneumatic stirrer, then Povidone is poured therein, in small amounts. Stirring is continued until dissolution.

Preparation of the Uncoated Lithium Carbonate Granules

One part of lithium carbonate is weighed and granulated in the granulator using the above described binder solution as granulation agent.

The humid granulate is passed through a 840 micron wire screen, dried at 40° C. for 15 hours in a forced air circulation thermostatized drier and subsequently the granulate is sieved through sieve with openings of 500 and 840 micron.

The powder and the granules smaller than 500 micron are regranulated with the same procedure as described above, but using water as binder. At the end of the granulation process, the granules are sieved through a sieve with openings of 500 and 840 micron.

The resulting granulate is weighed and placed in the stainless steel container of the coating pan. While it rotates at a suitable rate to ensure efficient rotation of the mass (about 12 rpm), the binder solution is sprayed on the granules by a spraying device and the lithium carbonate powder is added.

Spraying is carried out at intervals to provide better evaporation of the solvent, which is removed by an aspiration system, and to avoid any bubbles.

Finally, the granulate is sieved through a 1200 micron wire screen and dried at 40° C. for 15 hours in a forced air circulation thermostatized drier.

The granulate is sieved again through an 840 and 1200 micron mesh sieve.

Preparation of the Coating Film in Solution

Acetone and denatured ethanol are placed in the stainless steel container, ethylcellulose is added, with stirring. Stirring is continued until complete dissolution.

Coating of the Lithium Carbonate Granules

The lithium carbonate granules are placed in a fluidized bed and sprayed with the coating film.

Furthermore, small amounts of talc are poured onto the mass at the end of each spraying stage, to improve free-flowing of the mass.

At the end of the operation, granules are forced through a 1200 micron wire screen. After completion of the coating cycle, the granulate is dried.

Finally the granulate is sieved through sieve with openings of 840 and 1340 micron.

Capsule Filling

The lithium carbonate formulation is filled into hard-gelatin capsules by means of a capsule filling machine programmed to fill hard-gelatin capsules with the desired weight (mg) of granulate.

Filled capsules are closed and collected under continuous visual control in a double polyethylene bag placed in a tightly sealed metal container.

EXAMPLE 2

Bioequivalence Study on the OaD Lithium Carbonate 600 mg Capsule Formulation of the Invention Upon Single Administration Compared with the 300 mg Capsule Carbolithium® 300 Formulation Administered Twice Daily Experimental Protocol A two phases clinical trial has been designed and carried out according to the EEC guidelines for clinical trials on pharmaceuticals.

The study was carried out on 18 healthy volunteers.

Figure 2:
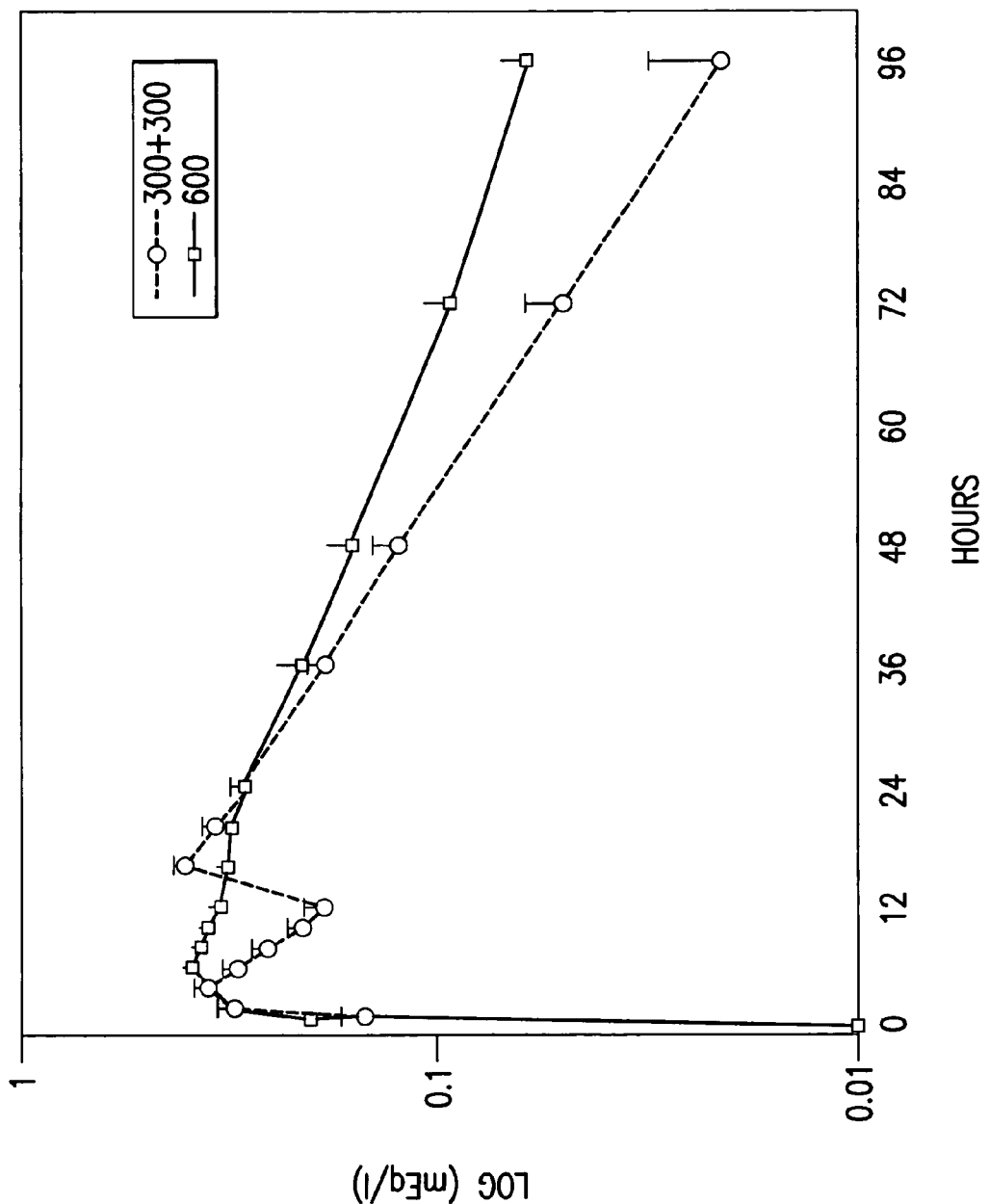

FIGS. 1 and 2 report the graphs based on the arithmetic means of the obtained results (each point is the mean of 18 measurements=patients).

Comments on the Results

The 300+300 mg lithium formulation covers the 24 hours with its two peaks, between which an about 50% fall occurs; the 600 mg OaD lithium formulation of the invention has Cmax slightly higher than the first peak of the 300+300 mg formulation, but after 24 hours the plasma concentration is reduced by 25% only. The lithium 300+300 mg formulation has plasma half-life of about 20 hours; the OaD lithium 600 mg formulation of the invention has half-life of about 36 hours. These data prove that the formulation of the invention is effective as expected, but that possible accumulation may occur after repeated administrations.

EXAMPLE 3

Bioequivalence Study on the OaD Lithium Carbonate 300 mg Capsule Formulation of the Invention Upon Single Administration Compared with the 300 mg Capsule Carbolithium® 300 Formulation upon Single Administration In order to better evaluate any accumulation risks, five healthy volunteers were subjected to single administration of the OaD 300 mg formulation of the invention in comparison with Carbolithium® 300 mg control formulation.

The lithium plasma concentration of each subject was monitored up to 72 hours, and urine lithium content up to 96 hours after administration was evaluated.

Figure 3:
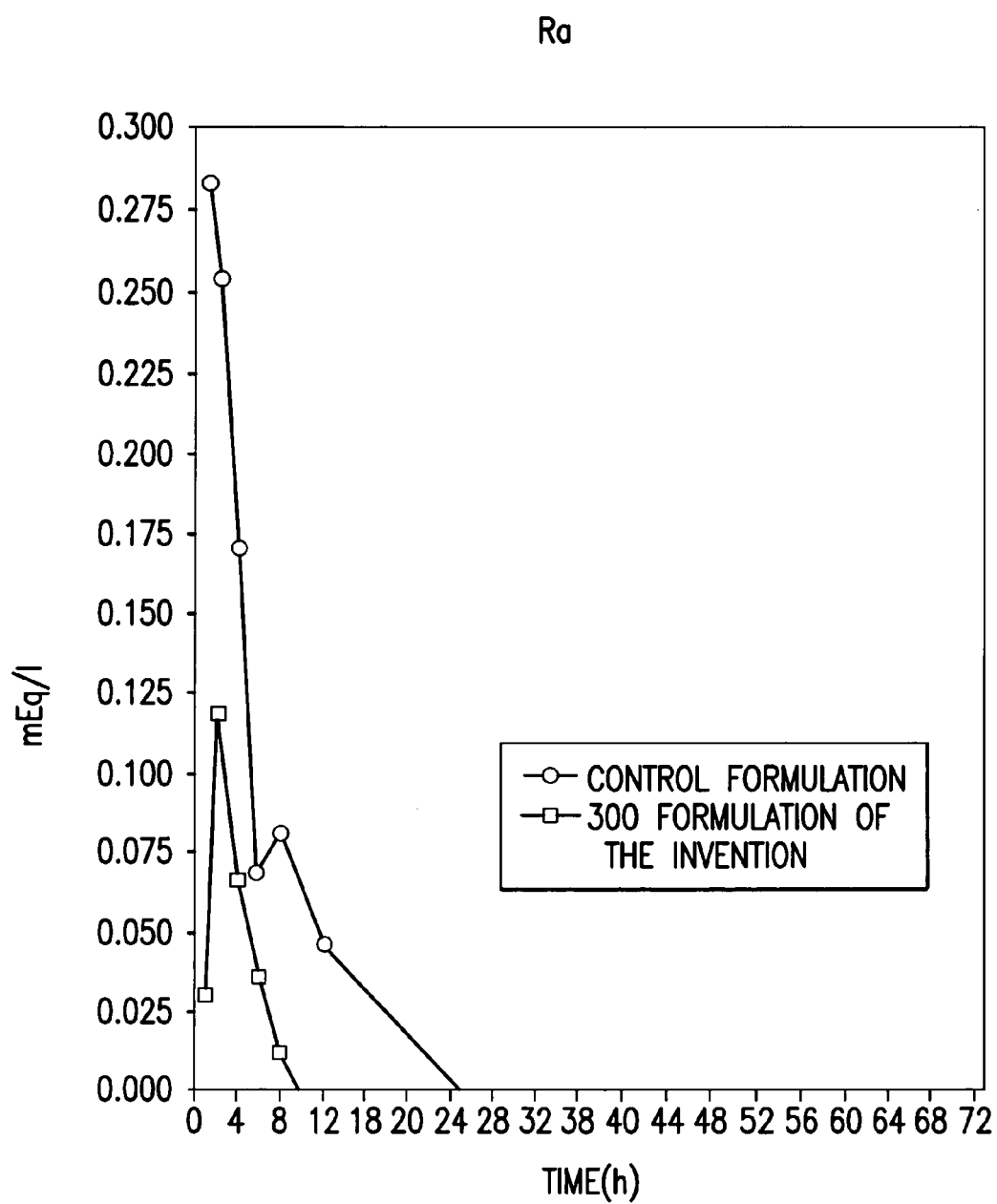
Figure 4:
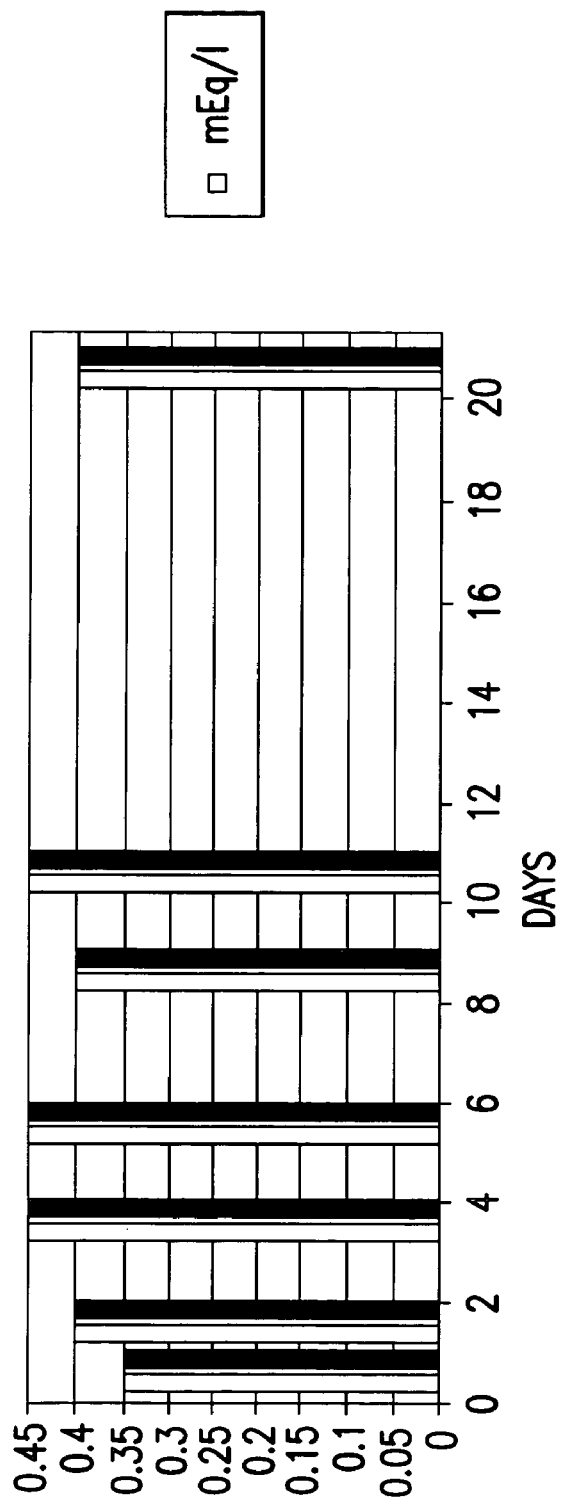

The graphs of FIGS. 3 and 4 disclose the results of the study.

Comments on the Results

1. The plasma lithium profile confirms the observations of the phase 1 study: the Cmax of the OaD formulation is half that of the Cmax of the control formulation, dosages being equal.

2. The Cmax of the control formulation is consistent with the known literature data.

3. After 24 hours, the plasma lithium concentration of both formulations is comparable (within the limits of the experimental fluctuations ascribable to the subjects).

4. The OaD formulation of the invention provides better therapeutic efficacy as it can be seen from the graphs of the phase I study since, without inducing toxic plasma peaks (one peak only, below the Ctox value, compared with two peaks of the control formulation), prevents the fall of lithium plasma concentration (to 50%) which always takes place between the two administrations of the control formulation.

5. Furthermore, considering 100 the urine lithium removed with reference to the single administration of the control formulation, it can be deduced that the lithium removal with the formulation of the invention is reduced by half.

6. Residual lithium does not circulate in blood (it is apparently absorbed by the tissues) neither contributes to induce accumulation.

These data are due to the chemical nature of the product and to the fact that lithium absorption, transport and elimination take place with a passive diffusion process and therefore with a rate which is linearly related with the originally available lithium concentration (upon administration). Therefore the administrations of lithium in low concentrations induce lower diffusion and elimination rates which, combined with the continuous release carried out by the OaD formulation of the invention, allows to attain a steady state with constant lithium plasma concentration and no risks of accumulation.

The results prove that when using the OaD lithium carbonate formulation of the invention, accumulation is most unlikely to take place, and the product can be considered both clinically effective and safe.

EXAMPLE 4

Clinical Trial with Repeated Administrations of OaD Lithium Carbonate Formulation A clinical trial has been carried out by administration of the lithium carbonate formulation of the invention, in the form of controlled release 450 mg (C.450 OaD) and 600 g (C.600 OaD) capsules, by single administration for 10 consecutive days to a group of 20 patients already under conventional therapy with lithium carbonate for a total of 20 days.

This trial aimed at verifying whether the formulations of the invention were capable of producing a constant plasma concentration of Li+ upon repeated administrations at the steady state without inducing accumulation and with peaks compatible with the determined safety dosages.

Figure 5:
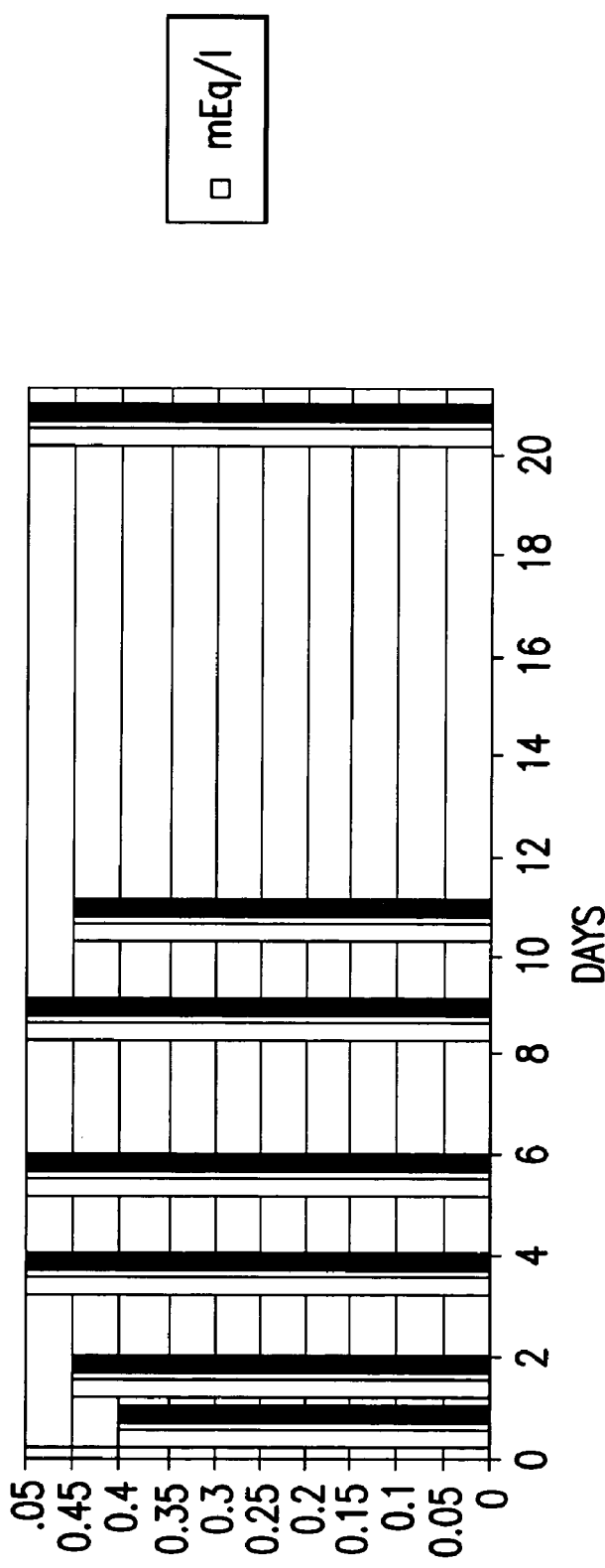

The results of this trial are expressed in the two graphs of FIGS. 4 and 5, corresponding to the two tested dosages.

FIG. 4: Lithium plasma concentration (each point corresponds to a mean of 20 patients) upon repeated administrations of 450 mg OaD formulation of the invention.

FIG. 5: Lithium plasma concentration (mean of 20 patients) upon repeated administrations of 600 mg OaD formulation of the invention.

Comments on the Results

The lithium plasma concentration profiles clearly show that:
  the OaD lithium carbonate formulation of the invention is therapeutically effective;
  the "therapeutical yield" is higher, as the subjects who had been stabilised with a therapeutical daily dose of 900 mg lithium carbonate conventional formulation maintained the steady state by single administration of the 600 mg OaD formulation;
  patients who had been stabilised with 600 mg of the conventional lithium carbonate formulation maintained the steady state by single administration of the 450 mg OaD formulation.

Therefore the OaD formulation of the invention is a therapeutically effective, safer formulation, and solves the problem involved by the rather low therapeutical index of lithium and can provide different dosages thus allowing to modulate the therapy according with the individual requirements of the patients.

The invention claimed is:

1. A controlled release once daily formulation for administration to a human patient, comprising coated granules of lithium carbonate, said formulation containing an amount of lithium carbonate from 300 mg to 900 mg per dosage unit, in the form of coated granules having the following composition by weight:
  93% to (150/1.161)% lithium carbonate;
  (2.575/1.61)% to 1.7% ethylcellulose;
  (1.125/1.61)% to 0.8% talc; and
  4.5% to (7.300/1.61)% polyvinylpyrrolidone.

2. The formulation of claim 1 wherein said amount of lithium carbonate is selected from the group consisting of 300 mg, 450 mg, and 600 mg.

3. The formulation of claim 1, wherein the coated granules are from about 840 microns to about 1340 microns in size.

4. The formulation of claim 1 wherein said granules have the following composition:
  93% lithium carbonate;
  1.7% ethylcellulose;
  0.8% talc; and
  4.5% polyvinylpyrrolidone.

5. The formulation of claim 1 wherein said granules have the following composition:
  (150/1.61)% lithium carbonate;
  (2.575/1.61)% ethylcellulose;
  (1.125/1.61)% talc; and
  (7.300/1.61)% polyvinylpyrrolidone.

6. A controlled release dosage formulation suitable for once daily administration to a human patient, comprising coated granules of lithium carbonate, said granules comprising by weight:
  93% to (150/1.161)% lithium carbonate;
  (2.575/1.61)% to 1.7% ethylcellulose;
  (1.125/1.61)% to 0.8% talc; and
  4.5% to (7.300/1.61)% polyvinylpyrrolidone.

7. The formulation of claim 6 wherein said granules have the following composition:
  93% lithium carbonate;
  1.7% ethylcellulose;
  0.8% talc; and
  4.5% polyvinylpyrrolidone.

8. The formulation of claim 6 wherein said granules have the following composition:
  (150/1.61)% lithium carbonate;
  (2.575/1.61)% ethylcellulose;
  (1.125/1.61)% talc; and
  (7.300/1.61)% polyvinylpyrrolidone.

9. The formulation of claim 6, wherein the coated granules are from about 840 microns to about 1340 microns in size.

* * * * *

UNITED STATES PATENT AND TRADEMARK OFFICE
CERTIFICATE OF CORRECTION

PATENT NO.       : 6,989,159 B2
APPLICATION NO.  : 10/343997
DATED            : January 24, 2006
INVENTOR(S)      : Tarro It is certified that error appears in the above-identified patent and that said Letters Patent is hereby corrected as shown below:

Claim 1, column 6, line 12, "150/1.161)%" should be -- 150/1.61)% --.

Claim 6, column 6, line 38, "150/1.161)%" should be -- 150/1.61)% --.

Signed and Sealed this

Eleventh Day of November, 2008

JON W. DUDAS
*Director of the United States Patent and Trademark Office*